Figure 1:
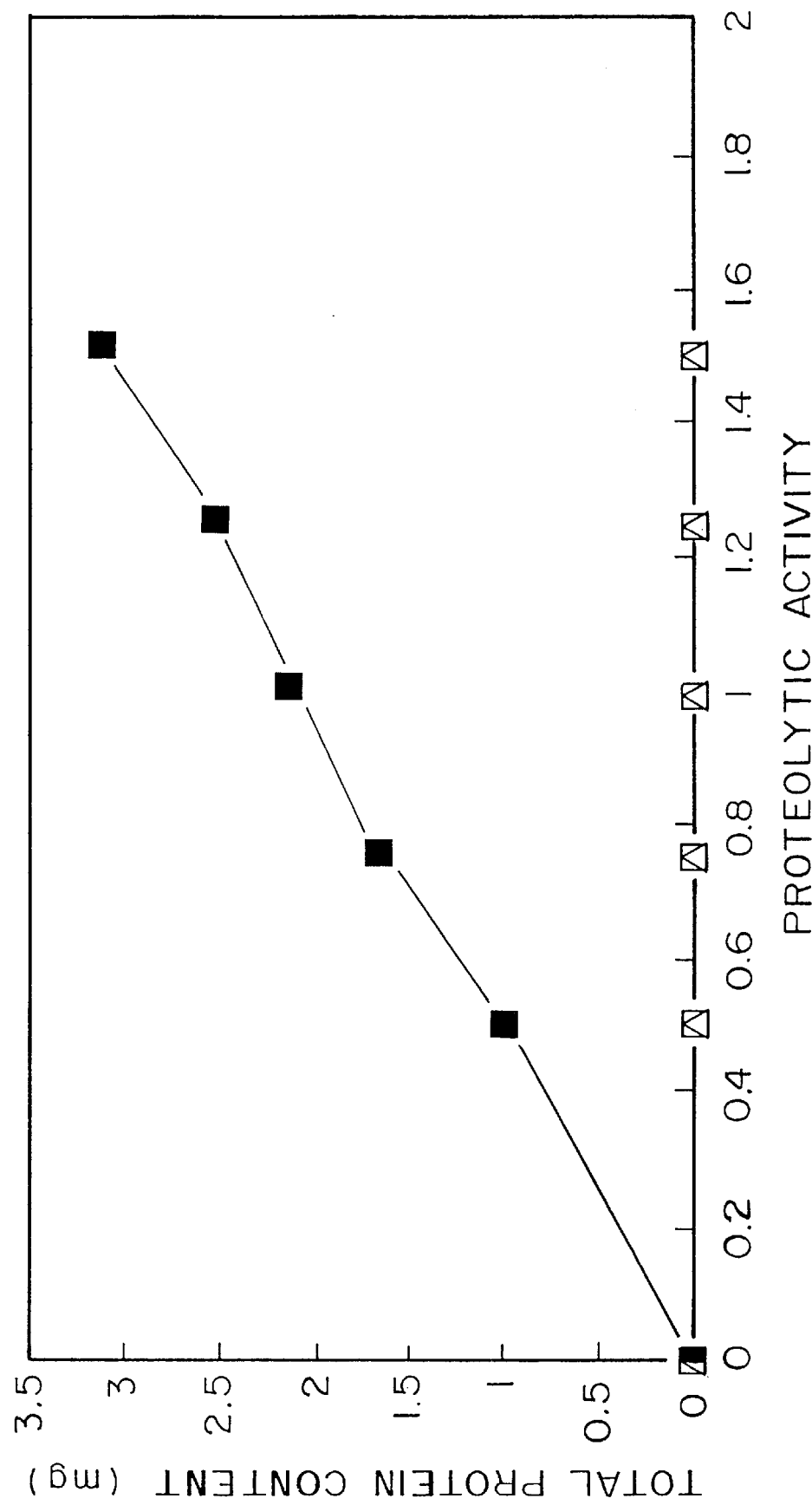

United States Patent [19]

Flores-Castañeda

[11] Patent Number: 5,861,263
[45] Date of Patent: *Jan. 19, 1999

[54] PREPARATION OF PRESERVED ENTAMOEBA HISTOLYTICA ANTIGENS WITHOUT ENZYMATIC INHIBITORS AND THEIR USE IN IMMUNOLOGICAL METHODS

[75] Inventor: Maria S. Flores-Castañeda, Monterrey, Mexico

[73] Assignee: Universidad Autonoma De Nuevo Leon, Monterrey, Mexico

[ * ] Notice: The term of this patent shall not extend beyond the expiration date of Pat. No. 5,459,042.

[21] Appl. No.: 480,184

[22] Filed: Jun. 7, 1995

Related U.S. Application Data

[63] Continuation-in-part of Ser. No. 139,290, Oct. 20, 1993, Pat. No. 5,459,042.

[30] Foreign Application Priority Data

Oct. 20, 1992 [MX] Mexico .................................. 926019

[51] Int. Cl.$^6$ .................. G01N 33/53; G01N 33/569; G01N 33/571
[52] U.S. Cl. .................. 435/7.22; 435/219; 435/7.36
[58] Field of Search .................. 435/7.22, 219; 23/253, 230 B

[56] References Cited

U.S. PATENT DOCUMENTS

| | | | |
|---|---|---|---|
| 3,963,441 | 6/1976 | Dietrich | 435/7.22 |
| 4,213,764 | 7/1980 | O'Connor | 435/7.36 |
| 4,762,789 | 8/1988 | Keene et al. | 435/219 |
| 5,272,058 | 12/1993 | Petri, Jr. et al. | 435/7.22 |
| 5,275,935 | 1/1944 | Stanley, Jr. et al. | 435/7.22 |
| 5,459,042 | 10/1995 | Flores de Castañeda | 435/7.22 |

OTHER PUBLICATIONS

Shiv Pillai, et al., *Gastroenterology*, 83, (1982), 1210–1214.
H.M. Mathews, et al., *J. Protozool.*, 33 (3), (1986), pp. 328–334.
R. Argüello-García, et al., *Arch. Invest. Méd.*, 21, (1990), pp. 3–9.
Salvador Said–Fernandez, et al., *Z. Parasite*, 56 (1978), 219–225.
Agneta Aust Kettis, et al., *Am. J. Trop. Med. Hyg.*, 32 (3), (1983), pp. 512–521.
Eva E. Avila, et al., *J. Protozool.*, 32 (1), (1985), pp. 163–166.
Kettis et al, Am. J. Trop. Med. Hyp. 1983, pp. 512–522.
Said–Fernandez et al, Z. Parasitenkunde, vol. 56, pp. 219–225, 1978.
Osorio et al, Parasitology, vol. 105, pp. 207–210, 1992.
Jain, U. et al, Indian J. Exp Biol, Dec. 1990, vol. 28 (12) pp. 1118–1123.
Prasad, R et al, Mol. & Biochem. Parasitology, vol. 56, pp. 279–288, 1992.
Robert, R. et al, J. of Clin. Microbio., Jun. 1990, vol. 28(6), pp. 1422–1424.
Shetty, N.P. et al, J. Clin. Pathol. 1990, vol. 43, pp. 950–952.
Parija, SC et al, Southeast Asian J Trop. Med. Pub. Health, Jun. 1991, vol. 22(2) pp. 249–253.
Morris, MN et al, S.A. Med. Journal, 30 Oct. 1971, vol. 45 #42 pp. 1206–1208.
Schulz, TF et al, Trop. Med. Parasitol, Sep. 1987, 38(3), pp. 149–52.
Joyce, MP et al, Am. J. Trop Med Hyg, Jan. 1988, 38(1), pp. 74–80.
Ricketts, A.P, Exp. Parasitol, vol. 74, 1992 Jun., pp. 463–469.
Shetty, N. et al, Arch. Invest. Med, 1990, 21(Suppl.1), pp. 41–46.
Arturo, C et al, Arch. Invest. Med, 1990, 21(Suppl 1) pp. 97–101.
Hock, G. M. et al, So East, Asian J of Trop. Med & Pub Health, vol 20(3) pp. 407–414, 1989.

*Primary Examiner*—James C. Housel
*Assistant Examiner*—Ginny Allen Portner
*Attorney, Agent, or Firm*—Foley & Lardner

[57] ABSTRACT

The method of the invention relates to the preservation of a complex antigenic system of *Entamoeba histolytica* molecules, without using enzymatic inhibitors and using these preserved *Entamoeba histolytica* molecules as a reagent in a diagnostic assay system and as a starting material for the isolation of *Entamoeba histolytica* proteins.

18 Claims, 12 Drawing Sheets

PREPARATION OF PRESERVED ENTAMOEBA HISTOLYTICA ANTIGENS WITHOUT ENZYMATIC INHIBITORS AND THEIR USE IN IMMUNOLOGICAL METHODS

This is a Continuation-in-Part of U.S. patent application Ser. No. 08/139,290 filed on Oct. 20, 1993, now U.S. Pat. No. 5,459,042.

BACKGROUND OF THE INVENTION

Amebiasis is a parasitic disease provoked by the protozoan *Entamoeba histolytica*. It affects mainly the inhabitants of developing countries. Under appropriate conditions, which are not well known, trophozoites differentiate into an ineffective form or cyst, which is present in excrements and by this route can infect a new host by oral ingestion of food and water or person to person transmission. Most of the people infected with *Entamoeba histolytica* are asymptomatic, but in 10% of the people with amebiasis, the protozoan produces sickness when it invades the intestinal mucosa producing amoebic colitis or more dangerous damage when the protozoan is extraintestinal and there is a dissemination of the protozoan to the liver, provoking an amoebic liver abscess. In the cases in which there is a perforation of the liver or the intestine, it can provoke pleural damage, pericarditis, peritonitis and even death. Amebiasis occupies the sixth place among the most frequent causes of death in Mexico. In Mexico as in Venezuela, 2% to 15% of the cases of children with diarrhea who have been hospitalized, have infections associated with an *Entamoeba histolytica*.

To conduct correct epidemiological studies, it will require the development of diagnostic methods which are sensitive and specific. The coproparasitoscopic diagnosis of *Entamoeba histolytica* is especially difficult, because it requires highly skilled workers to prevent false interpretations. The serologic diagnosis is not effective because the existing tests are not sensitive enough, especially when they are used in highly endemic zones. To obtain useful diagnostic tests, it is necessary to know the amoebic molecules that are actively involved in the cases of invasive amebiasis and to utilize these molecules to design effective diagnostic tests. Once the role of these molecules is known, studies can be performed to determine their involvement in the immune protection mechanisms generated against amoebas and the possible implementation of vaccines.

A major impediment to achieve this goal is the highly elevated enzymatic activity of the proteases present in the amoebic extracts (see McLaughlin et al., *Canadian Journal of Microbiology*, 23: 420–425 (1977), and Perez-Monfort, et al., *Molecular and Biochemical Parasitology*, 26: 87–98 (1987)). The proteases degrade proteins in the amoebic extracts by producing degradation products and making it impossible or at least very difficult, to standardize the methods of analysis of the antigenicity of these proteins. To prevent this enzymatic activity, enzymatic inhibitors have been used; however, because these inhibitors are not completely effective protein degradation continues. Generally, amebic extracts containing enzymatic inhibitors only permit working with extracts for relatively short periods of time and they do not provide the opportunity to store the same samples for later tests. A later study by Arguello-Garcia et al., *Arch. Invest. Med. (Mex.)* 21: 3–9 (Supl. 1) (1990) reported evaluating *E. histolytica* antigens utilizing different protein extraction methods. The highest yield of proteins from *E. histolytica* cell lysates was obtained by homogenizing trophozoites in the presence of 10 mM p-hydroxymercuribenzoate (pHMB) and by lysis with Triton X-100 and a mixture of protease inhibitors. Frozen extracts were found to be stable for a period of two or three months. However, these extracts were not subjected to repeated freezing and thawing (personal communication). The authors found that different methods for preparing amebic extracts resulted in differences in protein yields as well as antigenic composition as observed by electrophoretic patterns and that there was a need to select a standardized procedure for preparing amebic extracts for use in serological assays.

The present invention utilizes a method for preparing amebic extracts based upon the method described in Said-Fernandez et al., *Zeitschrift fur Parasitenkunde*, 56: 219–225 (1978), which removes lipids from amebic extracts. This method disloses that the electrophoretic analysis of total proteins from trophozoites of four different strains of the histolytica group of Entamoeba show a striking similarity between the two *E. histolytica* strains studied. The authors state that protein electrophoretic analysis can be used as a taxonomic criterion after confirming its use in a sufficiently large number of strains.

The present inventor has determined that amoebic antigens prepared by this method exhibit very low levels of proteolytic enzymatic activity which does not cause protein any extensive and interfering protein degradation. Amebic extracts prepared by this method are stable for at least six months without any enzymatic degradation. Therefore, antigens made by this method for use in diagnostic tests, such as ELISA or IHA, are stable for longer periods of time than extracts containing protease inhibitors. The longer shelf-life provides advantages for a commercial diagnostic product amebic antigens prepared according to this method.

The present inventor has recognized that amebic extracts produced according to this method could be utilized as a stable antigen in a diagnostic test, such as an ELISA or IRA, without utilizing protease inhibitors to prevent the degradation of the amebic extract which is the standard treatment in the prior art. Therefore, the present invention is directed to a diagnostic test and method for detecting the presence of antibodies to *E. histolytica* in a patient sample.

Further, the present inventor has recognized that amebic extracts produced according to this method could also be utilized as a starting material to produce and characterize specific *E. histolytica* proteins associated with different clinical manifestations of amebic disease; e.g., amebic liver abscesses (ALA) and intestinal amebiasis (IA). These specific proteins may be utilized as stable antigens in diagnostic tests, such as ELISA and IHA for detecting the presence of antibodies to *E. histolytica* in patient samples or further utilized in the production of a vaccine against *E. histolytica*.

SUMMARY OF THE INVENTION

The method of the invention relates to the preservation of the antigens of a certain microorganism without using enzymatic inhibitors, although, by no means restricted to *E. histolytica*. The enzymatic activity of the proteases which are contained by *E. histolytica* makes the study of the antigenically important amoebic molecules difficult. This is why one of the objectives of the present invention is to use *Entamoeba histolytica* as a model for other parasites.

Another objective of the present invention is to reduce the proteolytic action of the enzymes of the protozoan without adding enzymatic inhibitors.

A further objective of the present invention is to provide a superior amebic extract containing preserved *Entamoeba histolytica* antigens for studying amebic proteins. The present invention compares the amebic extract obtained with the method of the present invention with amebic extract obtained with conventional methods in which enzymatic inhibitors are used.

The present method is based on obtaining preserved *E. histolytica* antigens from an insoluble amoebal extraction with polar solvents or their mixtures and heating the extract in a boiling water bath for 5 to 20 minutes to obtain a greater reduction in enzymatic activity than that attained with enzymatic inhibitors. The procedure of the present invention preserves the antigenicity of the amoebal molecules, since they are recognized by the antibodies present in the sera of individuals with amoebic liver abscesses. The procedure can be of great help in the analysis and identification of antigenic molecules of amoebas and the study of the immunologic response against *Entamoeba histolytica*, but also it has many uses: for example, but not restricted to obtaining amebic molecules to prepare a vaccine, or to prepare diagnostic kits for the detection and aiding in the diagnosis of amebiasis, invasive or non-invasive, allowing appropriate treatment of these diseases.

The present invention provides a diagnostic composition, a kit and method of using the kit to detect the presence of antibodies to *E. histolytica*. The preserved *E. histolytica* antigen preparation identified as IC:MC, the insoluble fraction from *E. histolytica* trophozoites from an extraction with a mixture of chloroform and methanol which is subsequently heated, is utilized as the antigen in the diagnostic composition contained in the kit. The English version of the abbreviation for the antigen preparation is C:MIH derived from chloroform: methanol insoluble heat. Heat in Spanish is calentamiento, thus the original designation of IC:MC.

Alternatively, the antigen utilized in the diagnostic kit can be an 8–12 kDa protein obtained from preparative SDS-PAGE gels of either an IC:MC preparation or of media in which *E. histolytica* were cultured. The present invention provides a method for purifying the 8–12 kDa protein from SDS PAGE gels.

BRIEF DESCRIPTION OF THE DRAWINGS

FIG. 1 represents a graph in which the relationship between the protein content of the crude extracts and its proteolytic activity on azocasein is analyzed and is compared with the IC:MC fraction in the presence and absence of 2% SDS and 5% 2-ME. The figure depicts the activity of crude extract ■-■, IC:MC □- □ and, IC:MC+2% SDS and 5% 2-ME (2-mercaptoethanol) Δ-Δ. The activity of 0.5 mg crude extract protein is normalized to the unit (Unit=0.320 O.D).

FIG. 2 shows I. Electrophoretic patterns in SDS-PAGE. II.—Electroimmunotransfer blot (EITB) immunoelectrotransference patterns using serum from a patient with amebic liver abscesses (ALA). A. IC:MC fraction. B. amebic crude extract. C. Amebic crude extract with iodoacetamide inhibitor.

FIG. 3 shows the patterns of trophozoite extracts of *Entamoeba histolytica* HK-9. I. Electrophoretic patterns in gel of polyacrylamide-SDS stained with silver nitrate. II. EITB patterns, using the serum of a patient with amoebic liver abscess. A. Amebic crude fraction. B. IC:CM extract.

FIG. 4 shows the EITB patterns obtained with the anti-amoeba antibodies present in the sera of individuals with amebiasis. Amebic liver abscess (ALA) 3, 4, 6, 11, 12 and 15; Amebic Dysentery (AD) 8 and 9; Intestinal amebiasis (I.A.) 1, 2, 10, 13 and 14; Negative control sera. 5 and 7.

FIG. 5 shows protein bands and particularly the 8–12 kDA band separated by SDS-PAGE and an EITB (Immunoelectrotransference) using serum from an ALA patient. A and B—molecular weight makers; C—unused culture medium; D and F—used culture medium after *E. histolytica* growth; E- unused culture medium with bovine serum and proteins; G—bovine serum and H—IC:MC.

FIG. 6 shows an EITB from of an electroluted 8–12 kDa protein band from a preparative SDS-PAGE in both lanes A and B.

FIG. 7 shows an isoelectrofocusing test performed on the electroluted fraction polyacrylamide gels with a pH range from 3.5 to 10.0. A to G—known pI markers and H—protein bands obtained from preparative SDS-PAGE electroelution.

FIG. 8 shows the antigenic stability of the IC:MC fraction after incubation with buffers at different pHs. A—pH 6.8; B—pH 10.0; C—pH 9.0; D—pH 5.0; E—ph 3.0; F—molecular weight markers.

FIG. 9 shows an EITB of ammonium sulfate precipitations of IC:MC and used culture medium after *E. histolytica* growth. A—molecular weight markers; B—culture medium supernatant; C—culture medium precipitate; D—culture medium after *E. histolytica* growth (control); and E—IC:MC (control).

FIG. 10 shows an EITB of the 8–12 kDa protein precipitated by ammonium sulfate. A—80% precipitate; B—80% supernatant; C—70% precipitate; D—70% supernatant; E—60% precipitate and F—60% supernatant.

FIG. 11 shows an EITB SDS-PAGE gel of supernatants for different protein concentrations of culture medium after *E. histolytica* growth precipitated by rivanol. A—proteins at 14% rivanol; B—proteins at 7% rivanal; C—proteins at 3.5% rivanol; and D—molecular weight markers.

FIG. 12 shows and EITB of culture medium after *E. histolytica* growth passed through ionic exchangers. C—SP-Sephadex and D—DEAE-Sephadex.

DETAILED DESCRIPTION OF THE INVENTION

In the present invention procedure trophozoites of the strain *Entamoeba histolytica* HK-9 were used which were cultured initially and provided by Dr. Salvador Said-Fernandez of Centro de Investigaciones Biomedicas del Noreste del Instituto Mexicano del Seguro Social (IMSS). The trophozoites were cultured axenically as has been described by Said-Fernandez et al. (*Transactions of the Royal Society for Tropical Medicine and Hygiene*, 82: 249–253 (1988)). The trophozoites were used immediately or were lyophilized and stored until use. The protein contents was determined according to the method of Lowry et al.(*Journal of Biological Chemistry*, 193: 265–276 (1951)).

The extract which contains the insoluble fraction in polar solvents or their mixtures (chloroform, methanol, ether, ethanol) was obtained. The polar solvent insoluble fraction can be obtained by treating trophozoites with a polar solvent, such as chloroform, methanol, ethanol, ether or mixtures thereof. Preferably, the trophozoites are resuspended in ranges comprising between 5 to 100 volumes of chloroform-:methanol in a volume proportion comprising between 1:1 to 20:1 and inclusively 1:20. The mixture is stirred, centrifuged for at least two minutes at 400×g at 4° C. The supernatant is discarded and the operation can be repeated several times. When the fraction IC:M is obtained, it is vacuum dried and frozen minimally at −20 C. until its use. When ready to use, the IC:M fraction is resuspended in a buffer with pH ranging from 4 to 9, and it is heated in a boiling water bath, for several minutes to a maximum of 20 minutes. The treated IC:M fraction forms the IC:MC fraction, which is ready to use and may be preserved at −70°, −20° C. or 4° C. If the IC:MC fraction is freeze-dried or lyophilized, it can be stored at −70°, −20° C. or 4° C. for up to three years without enzymatic degradation of the proteins. If the IC:MC fraction is kept frozen in solution at −70° or −20° C., it can be stored for up to three years without protein degradation. Additionally, the preparation can be repeatedly frozen and thawed without protein degradation.

As established in the objectives; the reduction in proteolytic activity in the IC:MC fraction in absence of enzymatic inhibitors was demonstrated and the method of the present invention was compared with the conventional methods using an enzymatic inhibitor (iodoacetamide) to reduce the proteolytic activity of crude amoebic extracts. The crude extract was useful as a positive enzymatic activity control. To obtain crude extracts, the trophozoites were resuspended and diluted to a concentration of 5 mg/ml protein or more; the mixture was stirred and subjected to ultrasonic vibration; and then centrifuged at 400×g for 5 minutes, the sediment was discarded and the supernatant was used in the experiments.

There were 2 methods used to determine the proteolytic activity in the crude extracts and in the IC:MC fraction. In the first method, the substrate azocasein was used and the second method, hide power azure was used. In the first method the experiments were based on the reports of McLaughlin et al., *Canadian Journal of Microbiology*, 23: 420–425 (1977) and Avila et al., *Journal of Protozoology*, 32: 163–166 (1985). The crude extract was resuspended to a protein concentration of 25 mg/ml in 0.05M Tris-HCl, pH 7.6 at a range comprising of 1:1 to 10:1 and also 1:20 with 0.5% Triton X-100 and was incubated 1 hour at 4° C. The samples were centrifuged at 400×g for 2 minutes and the supernatants were recovered for analysis. The IC:MC fraction was treated the same way as the crude extract. To some of the samples, 2% of SDS and 10% of 2-ME were added. These samples were used in electrophoretic techniques on polyacrylamide gels in the presence of sodium dodecylsulphate (SDS-PAGE). Avila et al. (1985) have reported that SDS and 2-ME stimulate the proteolytic activity of the amoebic enzymes. With each sample of the different extracts, serial dilutions were made from 0.5 to 1.5 mg of total proteins with 150 $\mu$l of 0.05M Tris-HCL pH 7.5 and 100 $\mu$l 1% azocasein were added, and incubated for 90 minutes at 37° C. 250 $\mu$l of 10% trichloroacetic acid were added to each probe and centrifuged at 7000×g for 6 minutes. To each 200 $\mu$ls of supernatant 1.8 ml.5N NaOH was added and the absorbance of each sample was read at 420 nm on a PMQ II Zeiss PMQ III spectrophotometer (Zeiss, Germany). Trypsin was used as a positive control (300 ug for each reaction mixture).

FIG. 1 shows that the proteolytic activity of the crude extract on casein corresponds to a linear relationship with respect to the total protein content. In contrast, with the protein content of the crude extracts equivalent to that of the IC:MC fraction, there was no observed enzymatic activity, not even in the presence of SDS and 2-ME.

The second method was carried out according to Rinderknecht et al., *Clinica Chimica Acta.*, 21: 197–203 (1968). The activity corresponding to 6 million trophozoites was tested. Crude amebic extracts, IC:M and IC:MC were used. The samples were resuspended in 1.5 ml 0.05M Tris-HCL pH 7.5 containing 0.5% Triton X-100, and incubated for one hour at 4° C. and centrifuged at 11,000×g for 15 minutes. One ml. of the supernatant was added to 1 ml Tris-HCl containing 5 mg hide powder azure and 100 $\mu$l .2M cysteine. The samples were incubated at 37° C. for 1 hour and at the end of which the reaction was stopped by putting the tubes in an ice water bath. They were cold-centrifuged for 5 minutes at 450×g. The absorbency of the supernatants were determined at a wavelength of 600 nm. The former treatment was also done with samples that were incubated in the presence of SDS 2% or 2-ME 5% or 4 mM iodoacetamide. The positive control was taken as the activity obtained with 0.23 mg papain, which was activated with 0.7 mM 2-ME in Tris-HCl 0.05M at pH 8.0 at 4° C. for 10 minutes and then at 37° C. for 15 minutes with frequent stirring. Reaction mixtures without extracts were used as the negative control.

Using the insoluble substrate hide powder azure (Table 1), the activity of the crude extract was inhibited approximately 70% with 4 mM iodoacetamide. On the other hand, the IC:M fraction showed a reduced proteolytic activity of 87% to the crude extract activity. The IC:M fraction presented a slight increase in proteolytic activity in presence of 2% SDS and 5% 2-ME (0.322 units). As can be observed in Table 1, the increase was almost totally eliminated when the IC:M fraction was previously heated for 5 minutes (IC:MC fraction) and the proteolytic activity was not increased even in presence of SDS and 2-ME.

TABLE 1

| TREATMENT | PROTEOLYTIC ACTIVITY UNITS (NORMALIZED) | ACTIVITY REDUCTION PERCENTAGE (a) |
|---|---|---|
| Crude extract | 1.00b$^{-2}$ | 00 |
| Crude extract + iodoacetamide | 0.33 + 0.02 | 67 |
| IC:M fraction | 0.08 + 0.06 | 92 |
| IC:M fraction + 2% SDS and 5% 2-ME | 0.32 + 0.14 | 68 |
| IC:M fraction heated (IC:MC) + 2% SDS and 5% 2-ME | 0.09 + 0.11 | 91 |

(a)Reference based on the crude extract activity.
b1.00 = 0.750 + 0.09 UOD (units of optical density)

The IC:MC fraction prepared according to the disclosed method of the present invention provides preserved antigens of *E. histolytica* which have none of the proteolytic degradation problems of the amebic extracts made by the prior art methods as shown in Table 1. The IC:MC fraction is stable when frozen in a freeze-dried state or in solution as discussed above; and can be used as an antigen in diagnostic assays for up to three years without proteolytic degradation which is an advantage over a commercially available, such as the amebiasis microassay made by Diamedix Co., Miami, Fla.

As a result of the stability of the IC:MC fraction, the present inventor has been determined that the IC:MC fraction is an excellent amebic antigen in immunoassays, such as in an ELISA and IHA. Antibodies against all of the antigens, even those recognized by negative patient serum, can be detected by the ELISA using IC:MC as the antigen. However, sera from ALA and AD patients have higher anti-*E. histolytica* titers than the negative control sera. The diagnosis is made after knowing the titers as well as the clinical symptoms. The ELISA using the IC:MC fraction is just another tool to help the physician diagnose the patient after taking tests as well as clinical symptoms into account.

The IC:MC fraction can be used in an ELISA as follows: The IC:MC fraction is obtained as set forth above, sonicated in a sonicator, centrifuged at 1100×g for 3–5 minutes and the supernatant was removed. The concentration of the supernatant containing the *E. histolytica* proteins was adjusted to between 25–250 μg/ml, preferably between 50 μg or 100 μg/ml in 0.1M acetate buffer, pH 5.0. Then wells of polystyrene microtiter plates were coated with 100 μl of the adjusted supernatant and allowed to dry. The microtiter plates can be coated and blocked to prevent non-specific binding according to methods well known to persons skilled in the art. Samples suspected of containing antibodies to *E. histolytica* were incubated overnight at 4° C. in a coated well. After the incubation, the plates were washed 3 times with a wash solution (0.1M PBS, pH 7.4 containing 1:1000 Tween 20). The plates were then incubated with 1% BSA in the wash solution for 2 hours at 37° C. to block the plates and prevent non-specific binding. Other blocking reagents can be used such as, gelatin or skim milk. The BSA solution was discarded and the plates were washed 3 times with the wash solution. Then the plates were incubated with for example, 100 μl/ml of horseradish peroxidase conjugate for 2 hours at 37° C. The conjugate was discarded and the plates were washed 3 times with the wash solution. The plates were incubated in the dark with 100 μl/ml of substrate and chromogen (for horseradish peroxidase use $H_2O_2$ and orthophenylendiamine O.P.D.) for 30 minutes. The color reaction was stopped with 40 μl if $H_2SO_4$ and the absorbance is read ad OD 492 nm. Any know combinations of enzyme conjugate, substrate and chromogen which are known to people skilled in the art can be used and the color reaction can be stopped with other reagents known in the art.

Table 2 below provides the results of testing 34 amebic liver abscess patient sera using an ELISA method expressed in EU/ml (ELISA units/ml.)

TABLE 2

| SERA (ALA PATIENTS) | 50 ug IC:MC extract/ml Sera dilution | | 100 ug IC:MC extract/ml Sera dilution | |
|---|---|---|---|---|
| | 1:100 | 1:120 | 1:100 | 1:120 |
| 1 | 74.11 | 110.24 | 70.44 | 78.62 |
| 2 | 126.62 | 120.35 | 106.85 | 113.72 |
| 3 | 33.40 | 32.10 | 30.37 | 28.49 |
| 4 | 64.27 | 55.54 | 52.77 | 60.42 |
| 5 | 47.99 | 40.44 | 48.64 | 46.56 |
| 6 | 110.74 | 99.99 | 100 | 109.56 |
| 7 | 100 | 99.99 | 99.99 | 99.99 |
| 8 | 32.44 | 61.19 | 26.77 | 36.60 |
| 9 | 118.08 | 118.12 | 99.82 | 174.40 |
| 10 | 66.81 | 48.39 | 48.22 | 45.58 |
| 11 | 106.84 | 93.10 | 87.29 | 95.97 |
| 12 | 90.22 | 100.13 | 91.13 | 106.33 |
| 13 | 84.79 | 99.86 | 88.00 | 82.84 |
| 14 | 96.97 | 123.96 | 109.96 | 118.27 |
| 15 | 114.98 | 109.12 | 107.44 | 115.30 |
| 16 | 103.05 | 98.62 | 93.14 | 96.43 |
| 17 | 57.15 | 74.19 | 70.03 | 70.38 |
| 18 | 87.33 | 75.70 | 75.94 | 77.37 |
| 19 | 56.47 | 58.76 | 29.53 | 45.18 |
| 20 | 82.81 | 82.60 | 72.45 | 92.92 |
| 21 | 82.91 | 92.7 | 73.40 | 80.34 |
| 22 | 71.90 | 71.17 | 60.04 | 68.33 |
| 23 | 76.65 | 77.8 | 76.24 | 78.16 |
| 24 | 93.15 | 98 | 90.95 | 100.7 |
| 25 | 63.93 | 68.81 | 84.63 | 61.41 |
| 26 | 44.94 | 67.17 | 65.54 | 55.93 |
| 27 | 98.41 | 103.41 | 95.44 | 103.43 |
| 28 | 117.69 | 116.28 | 120.85 | 117.4 |
| 29 | 127.69 | 90.15 | 120.80 | 153.82 |
| 30 | 58.50 | 50.36 | 44.20 | 33.49 |

TABLE 2-continued

| SERA (ALA PATIENTS) | 50 ug IC:MC extract/ml Sera dilution | | 100 ug IC:MC extract/ml Sera dilution | |
|---|---|---|---|---|
| | 1:100 | 1:120 | 1:100 | 1:120 |
| 31 | 58.73 | 58.96 | 46.45 | 56.99 |
| 32 | 101.107 | 113.39 | 94.75 | 99.60 |
| 33 | 43.97 | 33.50 | 35.10 | 37.86 |
| 34 | 42.21 | 28.10 | 30.31 | 41.35 |

EU/ml is calculated as follows:

$$\frac{\text{Calibrator} = 100}{\text{Calibrator Absorbance}} \times \text{Test sample Absorbance} = \text{Test Sample } EU/\text{ml}$$

The calibrator is a known positive serum and less than 50 EU/ml is a negative result for invasive amebiasis.

The ELISA test described above was used for identification of antibody isotypes to *E. histolytica* in 36 sera of ALA patients and in 10 negative control sera of healthy subjects. The ALA patients had a positive IRA test for anti-*E. histolytica*, clinical symptoms of ALA, and an ultrasound confirmed the presence of amebic liver abscesses. The negative control subjects had a negative IHA test for anti-*E. histolytica*, a negative coproparasitoscopic test and did not have amebiasis clinical symptoms.

TABLE 3

Comparative Means between ALA Sera Levels and Negative Control Sera

| Polyvalent Ig (Total Ig) | ALA Sera 3.5 times greater than Negative Sera |
|---|---|
| IgG | ALA Sera 2.03 times greater than Negative Sera |
| IgA | ALA Sera 4.08 times greater than Negative Sera |
| IgM | ALA Sera 1.48 times greater than Negative Sera |

The numbers to support these results show that ELISA nits of ALA anti-*E. histolytica* are greater than ELISA units of negative control anti-*E. histolytica*. The data shows that it is very important to measure IgG and IgA isotypes in amebiasis ELISAs to obtain the best test results and that measuring the IgM isotype should be avoided in endemic ameoba zones.

The IC:MC extract can also be used in an IHA (Indirect Hemagglutination Assay) to coat RBCs using diethylmethylcarboidimide as the coupling agent. The IC:MC coated RBCs were incubated with samples suspected of containing antibodies to *E. histolytica* in polystyrene microtiter plates and positive samples resulted in agglutination of the RBCs which could be visually detected.

The IC:MC fraction is also useful in studying the anti-*E. histolytica* induced in animal models, such as mice. The DOT-BLOT was used to detect anti-*E. histolytica* in sera of mice immunized with freeze dried *E. histolytica* trophozoites. The mice were immunized by intraperitoneal (IP) route or by the oral (OP) route. Nitrocellulose membrane sheet points were coated with the IC:MC fraction and incubated with mouse sera in 0.1M PBS, pH 7.4. The reaction bands were developed with a conjugate anti-mouse antibody, $H_2O_2$ and 3,3 diaminobenzidine. The DOT-BLOT results show that mice immunized intraperitoneally developed a greater immune response anti-*E. histolytica* than mice immunized by oral route.

Additionally the ELISA described above was used to determine the levels and identification of the isotypes of anti-*E. histolytica* in the sera of mice immunized with freeze dried *E. histolytica* trophozoites by intraperitoneal (IP) route or by the oral (OP) route. The results showed no difference in ELISA Units between the immunization routes for IgM and IgA and showed differences in ELISA Units between the immunization routes for IgG and polyvalent Ig.

The study of amoebic molecules is difficult because they are quickly degraded due the enzymatic activity of the proteases contained in *E. histolytica*. The present invention has verified that many parasite molecules are preserved. As a result of the electrophoretic analysis of the crude extracts, the crude extracts with iodoacetamide and the IC:MC fraction, it was demonstrated that the IC:MC fraction preserves a great variety of molecules of low, medium and high molecular weights, which were stained with silver nitrate. The crude extract and the crude extract with iodoacetamide contain enzymatic degradation products. The different extracts were electrophoretically analyzed in polyacrylamide gels with a linear gradient of 8–18% T 2.7C, in the presence of SDS with the modified Maizel technique (Maizel, JR., J. V. In: *Methods in Virology*, Vol. V, 198–246, Maramorosch, K. & Kaprowski, H (editors), New York: Academic Press (1971)). Briefly 5% packing gels were used. After a 20 minute pre-run at 50 V, 120 mg per cm of the amoebal extract (IC:MC) was applied in a 0.049M Tris-HCl buffer pH of 6.8 containing 10% glycerol, 2% SDS, 0.015% bromophenol blue and 5% 2-ME. In each run, known molecular weight markers which were reagents of reactive grade (R) were also run. After the run, part of the gel subjected to electrophoresis was separated to be stained with silver nitrate with modification to the Merril technique (Merril, C. R. et al. *Science*, 211, 1434–1438 (1981)). This portion of the gels were fixed with a 50% methanol: 12% acetic acid solution for 20 minutes; the gels were washed to eliminate the SDS excess with a 10% ethanol: 5% acetic acid solution, followed by three washings of 5 minutes each, with distilled water. Silver nitrate (0.02M) was added for 30 minutes. The bands were developed with 0.28M sodium carbonate with 0.05% formalin. The reaction was stopped with 1% acetic acid.

Figure 2:
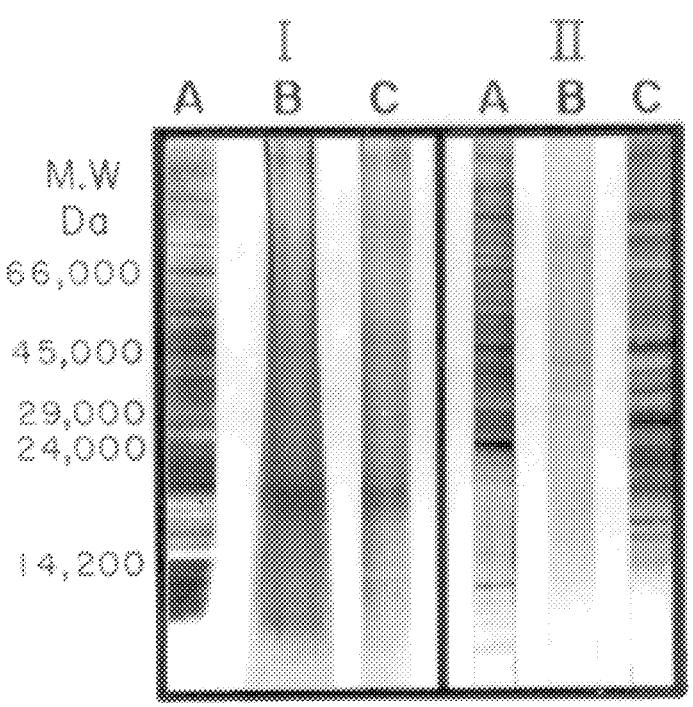

In FIG. 2, lanes IB and IC show the electrophoretic patterns corresponding to the crude extract and to the crude extract+iodoacetamide and lane IA corresponds to the heated IC:M fraction (IC:NC). The IC:MC fraction presents the best resolution with a great variety of bands of different molecular weights. In the lane of the crude extract (IB), there are only a few bands observed; but at the front of the run an important stain that contains low molecular weight peptides which come from the enzymatic degradation of higher molecular weight molecules was observed. The crude extract lane with iodoacetamide (IC) presents more bands than the crude extract alone, but even so, it presents fewer bands than the IC:MC fraction. The crude extract with the enzymatic inhibitor iodoacetamide must be used quickly, whereas the IC:MC fraction can be conserved for at least three years as discussed above.

The method of the present invention is directed to immunoassays utilizing preserved *E. histolytica* antigens contained in the IC:MC fraction which do not require using enzymatic inhibitors and to purification of the amebic proteins obtained from the IC:MC fraction.

One of the objectives of the present invention is the use of *Entamoeba histolytica* as a model to design a methodology to preserve the antigens of parasites and a further objective is to compare the preserved antigens of the present invention with the antigens obtained by conventional methods using enzymatic inhibitors. Therefore, a test to verify that the antibodies present in the sera of patients with amoebic liver abscesses (ALA) recognize and react with the molecules present in the extracts which are electrophoretically isolated, was performed. FIG. 2, II shows that the amebic molecules, which are electrophoretically isolated according to their molecular weight, were electrotransferred to a nitrocellulose sheet in an electrotransfer chamber (R) for 90 minutes at 1.0 amp final, according to Towbin et al. (*PNAS*, 76: 4350–4354 (1979)). After the transfer, the nitrocellulose membrane was blocked with 3% fish gelatin (R) in 0.15M PBD pH 7.4. The sera to be analyzed were diluted to 1:50 in PBS with 0.3% gelatin and Tween 20 (R) 1:1000 and were incubated with the nitrocellulose sheet over night at 4° C. This was developed with a polyvalent conjugate of total human anti-immunoglobulins bonded to peroxidase, in the presence of $H_2O_2$ substrate and 3,3 diaminobenzidine tetrahydrochloride as chromogen (R).

Also, it was demonstrated that the antigenic structure of the amoebal molecules is preserved in the IC:MC fraction obtained with the procedure described in this invention, since the antibodies of the sera of patients with amoebic liver abscesses (ALA) give antigen-antibody reaction bands with the electrotransfer preparations on nitrocellulose sheets (FIG. 2-II). More bands corresponding to antigenic reactions in the IC:MC fraction (FIG. 2-IIA) were observed than in the crude extracts (FIG. 2-IIB), in which only a few recognition bands were observed, since the major part of the antigens had been degraded by amoebic enzymes. Also more bands in the heated IC:M fraction (IC:MC) were observed than in the crude extract with iodoacetamide (FIGS. 2-IIA, 2-IIC). These results demonstrate that even in the presence of the inhibitor, many molecules are degraded, whereas they are preserved in the IC:MC fraction with the method of the invention.

Identification through imunoelectrotransfer of antigens of *Enritmoeb histolytica*, recognized only by sera of patients with invasive amebiasis Sera were obtained by venous puncture from 32 adults of both sexes who attended at "Dr. Jose Eleuterio Gonzalez" University Hospital, in Monterrey Nuevo Leon, Mexico. Aliquots were taken and frozen at −20° until use.

For this study the sera were classified in the following groups:

Group 1. (32 cases). In this group were included the sera of patients with amoebic liver abscess (ALA) with a clinical picture consistent with ALA; with echography also consistent with ALA and with positive IHA test.

Group 2. (21 cases). In this group the sera of individuals with luminal intestinal amebiasis (IA) were included with positive coproparasitoscopic test and without clinical symptoms. To select this group, 3 coproparasitoscopic serial tests were made from 554 university students.

Group 3. (15 cases). Negative control. The sera were chosen from individuals who met the following criteria: lack of amebiasis symptoms, negative serial coproparasitoscopic test and negative IHA test and without any evidence of having suffered from symptomatic amebiasis.

COPROPARASITOSCOPIC TEST TO CHOOSE THE INDIVIDUALS FROM GROUP 2 AND 3

ANALYZED POPULATION: 554 students of the Universidad Autonoma de Nuevo Leon were studied, whose ages ranged from 16 to 19, belonging to the lower income classes.
FECAL SAMPLES: Three serial fecal samples of each individual were collected and conserved in 5% formyl at 4° C. until their analysis under microscope.
METHOD USED: The Faust concentration and flotation method was used to obtain cysts, eggs and larvae of parasites. (Faust E. C. et al., *Parasitologia Clinica de Craig V Faust*. 2nd Edition, Mexico: UTEHA, 1056 (1961)).
ANTIGENS OF *Entamoeba histolytica*:

The trophozoites of *Entamoeba histolytica* strain HK-9, were cultured in a PHPS medium. (Said-Fernandez, S. et al., *Trans R Soc. Troy Med Hva*, 83: 29 (1988)).

AMOEBAL EXTRACTS: IC:MC fraction obtained according to the procedure of the present invention. The obtained IC:M fraction was vacuum dried and dissolved in 0.049M Tris HCl buffer pH 6.8, containing 10% glycerol, 2% SDS, 0.015% bromophenol blue. The sample was subjected to a boiling water bath for 5 minutes, then aliquots were frozen at −70° C. Prior to use 5% 2-mercaptoethanol was added.
POLYACRYLAMIDE GELS (SDS-PAGE) AND IMMUNOELECTROTRANSFERENCE (EITB): These experiments were performed as described above. DATA ANALYSIS: Each paper strip was examined individually and the migration distances were measured to calculate the Rf-value of each antigenic band. The molecular weights were calculated by interpolation on the obtained curves with commercially available markers of known molecular weight (Rf= distance of the protein migration/distance of the dye migration).
INDIRECT HEMAGGLUTINATION TEST (IHA): This was made according to commercial kit instructions (Behring). RBC coated with soluble Entameoba histolytica HK9 antigen can also be used in the IHA.

RESULTS

To select the sera of the individuals which would comprise groups 2 and 3 (intestinal amebiasis without symptoms and negative control), a serial coproparasitoscopic test of 554 students was made, and the results are shown in Tables 4 and 5. Ninety-four individuals presented *Entamoeba histolytica*, representing 13.35% of the analyzed population. To comprise group 2, sera of individuals only with *Entamoeba histolytica* were selected but those in which this protozoan was found with any pathogenic or commensal species were discarded for this study. (Flores-Castaneda M.S. et al. *Border Epidemiological Bulletin O.P.S.* (W.H.O. no. 5: 1–5 (1991)).

TABLE 4

RESULTS OF THE COPROPARASITOSCOPIC TESTS MADE IN 554 INDIVIDUALS

| RESULTS | NUMBER |
| --- | --- |
| NEGATIVE | 382 (69%) |
| POSITIVE FOR PATHOGENIC SPECIES* | 109 (19.7%) |
| POSITIVE FOR COMMENSALS | 63 (11.3%) |

*including *Entamoeba histolytica*

TABLE 5

PROPORTION OF THE INDIVIDUALS WITH POSITIVE COPROPARASITOSCOPIC FOR *Entamoeba histolytica*

| SPECIES | NUMBER OF INDIVIDUALS |
| --- | --- |
| *Entamoeba histolytica* | 36 |
| *Entamoeba histolytica* + Any pathogenic species (a) | 5 |
| *Entamoeba histolytica* + Any commensal species (b) | 53 |

(a) association with *G. lamblia* or *Hymenolepisnana*.
(b) association with *E. coli, E. nana, I. buetschlii*.

Figure 3:
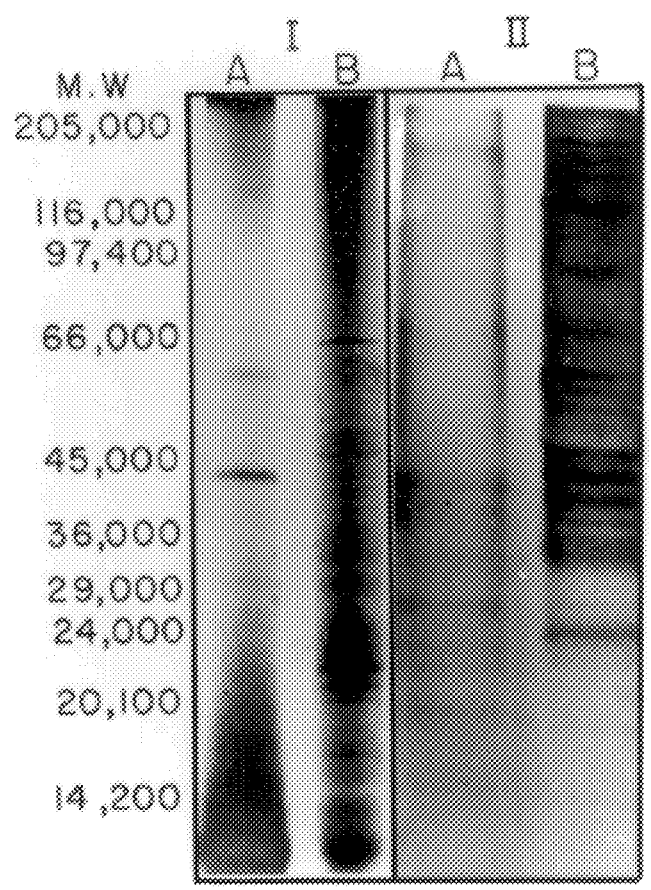

Electrophoresis in polyacrylamide gels (SDS-PAGE) were made, of *Entamoeba histolytica* crude extracts and the IC:MC fraction. The results are shown in FIG. 3. A better resolution was obtained with the IC:MC fraction, in the gels stained with silver nitrate (IB) as in the EITB (IB, IIB). In FIG. 3 (IB), it can be observed that the obtained electrophoretic pattern is very complex and presents bands of molecules with molecular weights between 8 kDa and 200 kDa. We also verified that not all the amoebic molecules are recognized by the serum of the patient with ALA used in this EITB (IIB compared with IB), which seems to indicate that not all the amoebic molecules are immunogenic. The *Entamoeba histolytica* proteases are very active; the spot which appeared at the front of the crude extract are random enzymatic degradation products, which are not observed in the IC:MC fraction.

Figure 4:
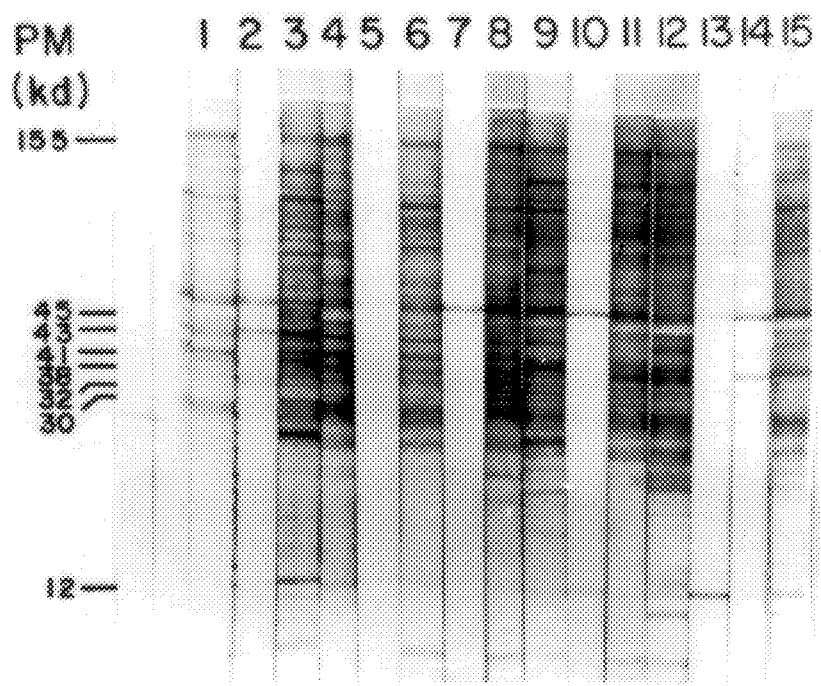
Figure 5:
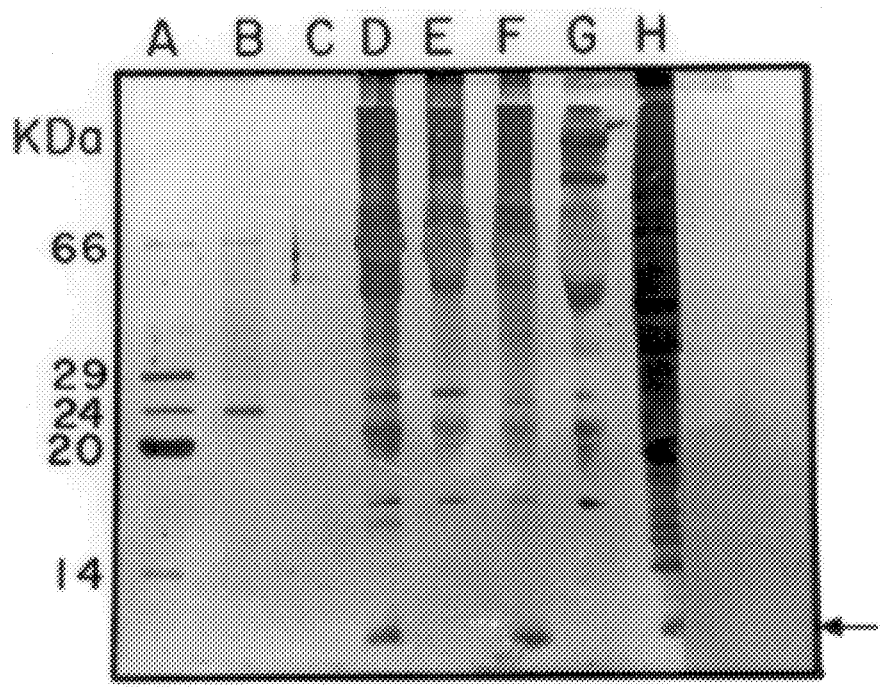
Figure 6:
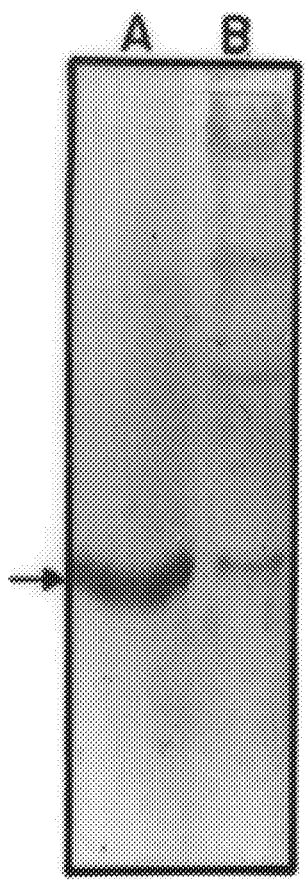

To determine the molecular weights relative to the immunodominant bands, the IC:MC fraction was analyzed by SDS-PAGE and EITB and the antigen-antibody reaction bands obtained with sera from Groups 1, 2, and 3 were correlated to the protein bands on the SDS-PAGE gels. From this data, antigenic reference patterns were identified for each group of sera. There was always a more intense reactivity with the ALA sera compared with that obtained with the IA sera (FIG. 4) was obtained. The IA sera and the negative control sera give reaction bands but weaker ones. This finding was expected because Mexico is an amebiasis endemic zone. The results allowed the identification of bands that are recognized by all the sera and have relative molecular weights of 45, 43, 42, 39, 38, 32, 31 and 12 kDas. Some bands are recognized only by the ALA and IA sera and have relative molecular weights of: 150, 29, 21, 20, 17, 16, 14, and 13 kDas. One of the most relevant aspects of the present invention is the identification of an antigenic pattern recognized exclusively and selectively by sera from amebic liver abscess (ALA) patients. The EITB pattern exclusive for ALA includes bands with molecular weights of 23, 25, 37, 11, 10, 9 and 8 kDas, which are only recognized by the sera of patients with amoebic liver abscesses. No sera of patients with IA recognized these bands (FIG. 4: lanes 1, 10, 13).

If it is assumed that only invasive amebiasis (ALA) induces protection against further amebic reinfections, it can be assumed that the antigens of the ALA EITB patterns may play an important role in immune protection against amoebas. The identified characteristic ALA-EITB pattern is useful to differentiate the invasive amebiasis (ALA) patients sera from those with non invasive intestinal amebiasis (IA). The EITB patterns could help our knowledge of amoebic antigens involved in induction of immune response against *Entamoeba histolytica*.

FURTHER PURIFICATION OF THE 8 kDa PROTEIN

One of the proteins which has been found to be associated with ALA sera using the EITB technique described above is the 8 kDa proteins identified in FIGS. 3–11; however, this protein band appears to be between 8–12 kDas with the various procedures, gels, and columns performed by the present inventor.

The 8–12 kDa protein band was obtained from a preparative SDS-PAGE gel using either the IC:MC fraction or used *E. histolytica* culture medium as the starting material. An EITB was performed as described above and FIG. 5 shows that the 8–12 kDa protein is present in lanes D, F, and H. Lanes D and F show the fractionated used *E. histolytica* culture medium and lane H shows the fractionated IC:MC.

From this preparative SDS-PAGE gel, the 8–12 kDa band was cut out and electroeluted and a partially purified fraction was obtained. To confirm that this fraction contained the 8–12 kDa protein, the partially purified fraction was again run on and SDS-PAGE gel an a Western Blot was performed using ALA patient sera (See FIG. 6) showing that the band that migrated had a molecular weight of 8–12 kDas.

Figure 7:
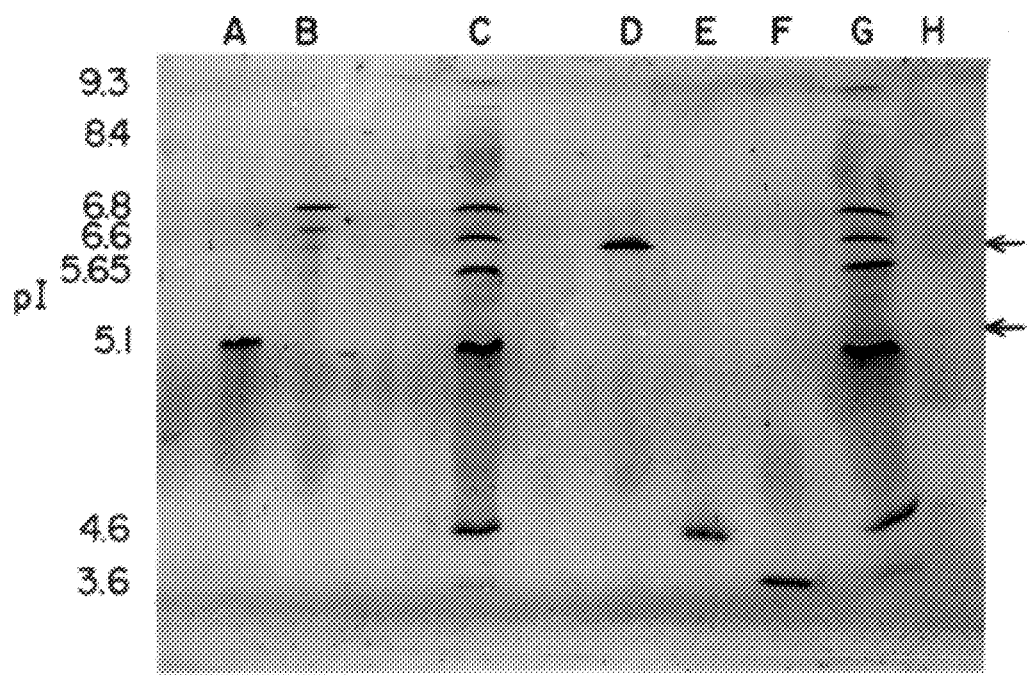
Figure 8:
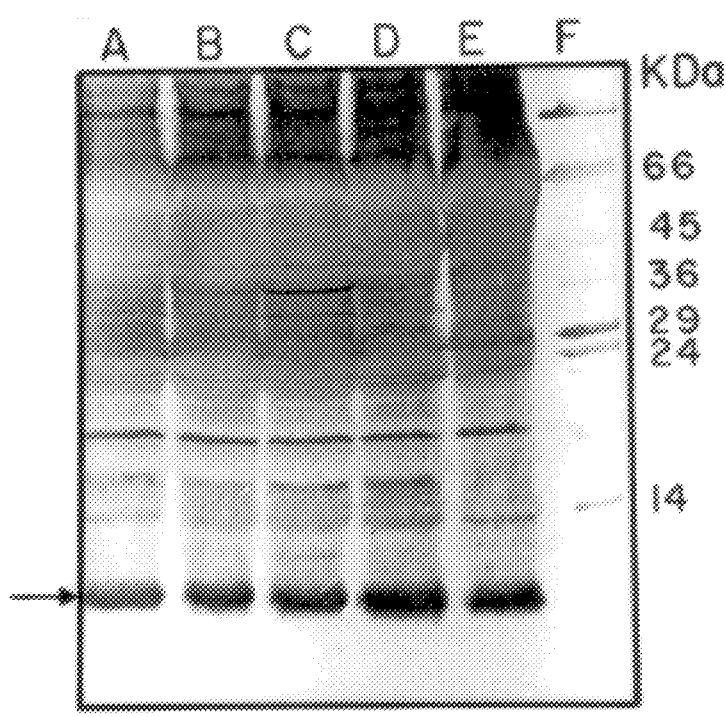

Isoelectric focusing was performed on the electroeluted fraction on a 5% polyacrylamide gel within a 3–10 pH range. In FIG. 7, lanes A–G represent known pI markers and lane H represents the electroeluted fraction after staining with Coomasie Blue. Two bands marked by arrows can be observed in lane H. The first band has a pI between pH 6.5 and 7.5 and the second band has a pI between pH 5.5 and 6.5. The isoelectrofocusing has also been performed in liquid phase from an IC:NC starting material (data not shown).

The IC:NC fraction was incubated in water, and various buffers, including acetate buffer, MES, phosphate buffer, NaCl, salt phosphate, Tris-HCl, HEPES, carbonates and bicarbonates at pHs of 10.0, 9.0, 8.0, 7.5, 7.0, 6.8, 6.5, 5.5, 5.0, 4.5, 3.6 and 3.0 for several hours. Then electrophoretic and immunoelectrotransfer or Western Blot was performed and positive antibody-antigen reactions were observed (see FIG. 8). This tested the antigenicity conservation of the antigen in different buffers at different pH values, water and different precipitating salts. It was found that the antigenicity was preserved because the antigen could be recognized by antibodies in ALA sera. The 8–12 kDa protein is shown with an arrow in lanes A–E.

Figure 9:
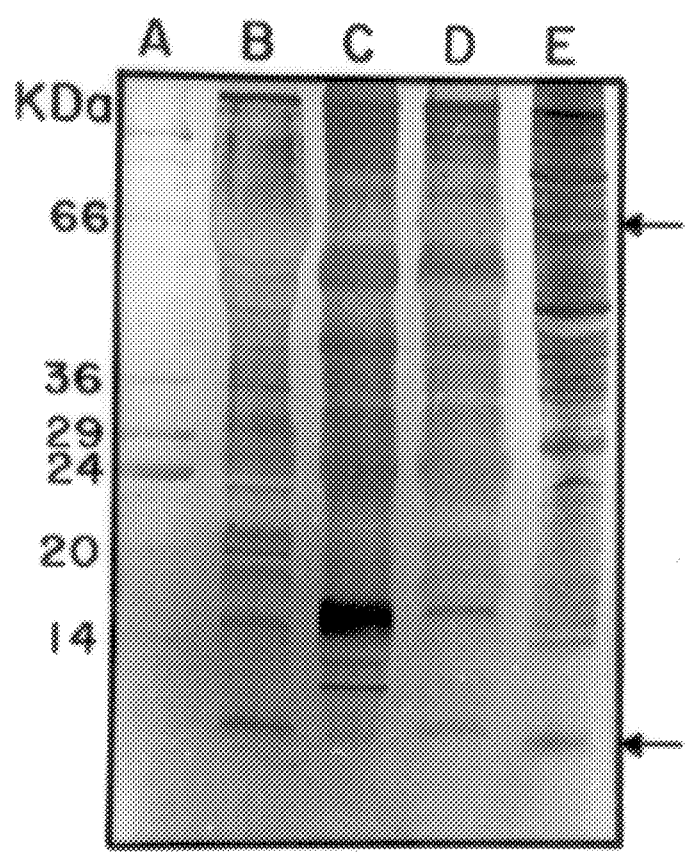
Figure 10:
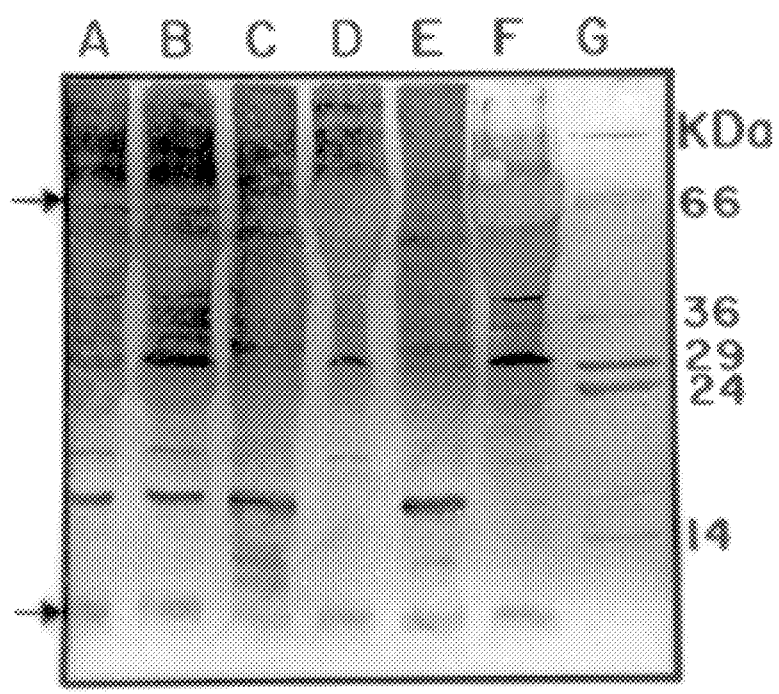

The culture media in which the E. histolytica grows as well as the IC:MC can be precipitated with ammonium sulfate at different concentrations as shown in FIG. 9. An 8 kDa band can be seen in lane B (used E. histolytica culture medium) and lane E (IC:MC). The 8–12 kDa protein can be precipitated with ammonium sulfate at 30, 50, 60, 70, and 80% and probably by sodium sulfate. FIG. 10 shows an EITB of the 8–12 kDa protein precipitated at 60, 70 and 80% and is present in both the precipitate and supernatant at each of these cuts.

Figure 11:
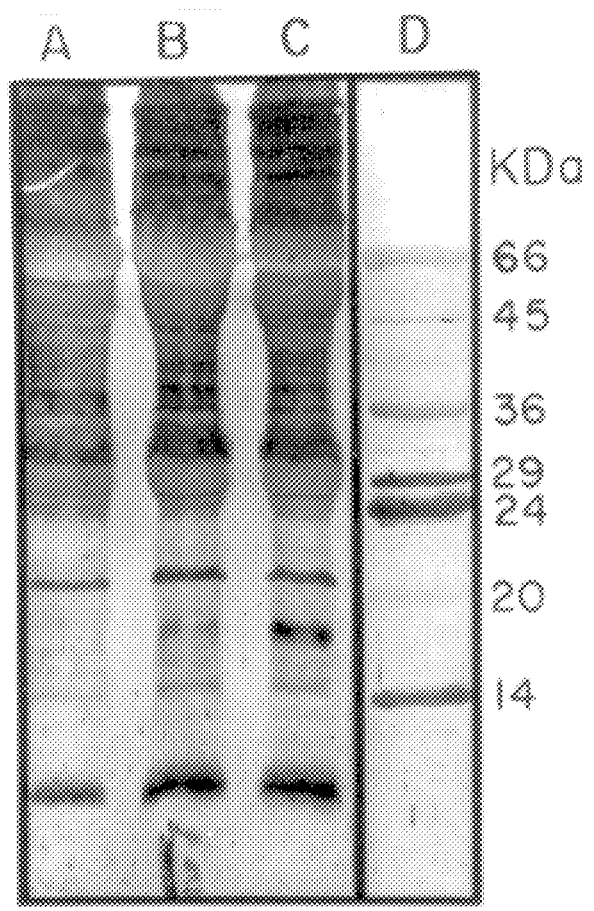

FIG. 11 shows an EITB SDS-PAGE gel of supernatants for different protein concentrations of culture medium after growth of E. histolytica which is precipitated by rivanol (6,9-diamino-3-ethoxy acridine lactate). This method precipitates out a large amount of albumin, which is in the culture medium and in IC:MC. It precipitates some of the 8–12 kDa protein but most of it stays in solution (see FIG. 11). Thus, this method could be used as a step to precipitate out unwanted proteins with the 8–12 kDa proteins remaining in solution.

Figure 12:
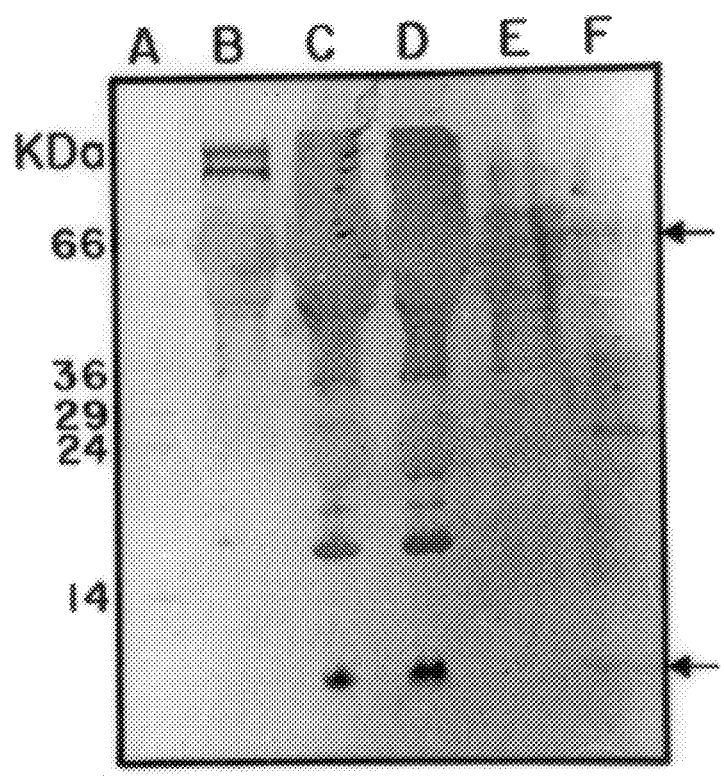

The 8–12 kDa protein can be bound to cationic or anionic exchange resins, such as, SP-Sephadex or DEAE-Sephadex (See FIG. 12).

The methods described above can be used to isolate the 8–12 kDa protein as well as other proteins of interest which can be separated and purified from the starting material, used Entamoeba culture media or IC:MC. These proteins and particularly the 8–12 kDa protein can be used as the antigen in diagnostic kits to investigate liver damage caused by Entamoeba and as the basis of a vaccine against Entamoeba.

The 8–12 kDa protein can be isolated from used culture medium from growth by E. histolytica by precipitating it with 3.5–14% rivanol. Taking the supernatant and dialysing it against distilled water or an appropriate buffer, such as Tris-HCl to concentrate the protein. Then the protein is loaded unto a preparative SDS-PAGE gel and electroluted to obtain a protein band between 8–12 kDas.

The IC:MC fraction can be loaded directly onto a preparative SDS-PAGE gel and electroluted to obtain a protein band between 8–12 kDas.

I claim:

1. A method of detecting antibodies to Entamoeba histolytica in a sample comprising:

incubating a diagnostic composition comprising preserved Entamoeba histolytica antigens (IC:MC) without the presence of enzymatic inhibitors, wherein said antigens are stable for at least six months, with a sample suspected of containing antibodies to Entamoeba histolytica for a sufficient period of time and under sufficient conditions to allow antibody-antigen binding; and detecting said antibody-antigen binding, wherein said preserved antigens are produced by:
        culturing trophozoites of Entamoeba histolytica axenically;
        lyophilizing said trophozoites;
        extracting an insoluble fraction from the trophozoites with polar solvents;
        drying the insoluble fraction to eliminate residues of the solvents;
        suspending the dried fraction in a buffer; and
        heating the buffered suspension for a sufficient time and at a sufficient temperature to yield said preserved Entamoeba histolytica antigens.

2. The method of claim 1, further comprising:

binding said preserved Entamoeba histolytica antigen of said diagnostic composition to a solid support prior to said incubating step; and detecting said antibody-antigen binding by adding a labeled antibody to said antibody bound to said antigen and measuring the presence of said labeled antibody.

3. The method of claim 1, further comprising:

binding said preserved Entamoeba histolytica antigen of said diagnostic composition to a solid support prior to said incubating step; and detecting said antibody-antigen binding by visually observing agglutination of said antigen bound to said solid support.

4. The method of claim 2, wherein said labeled antibody is selected from the group consisting of a polyvalent anti-human antibody, an anti-human IgG, an anti-human IgA, and a combination of anti-human IgG and anti-human IgA.

5. The method of claim 2, wherein said method is an ELISA and a negative result for invasive amebiasis is determined by comparing the result of a known negative amebiasis control serum with the result from said sample and assigning a known positive serum the value of 100.

6. A method of determining an antigenic reference pattern of proteins selectively recognized by sera from patients having invasive amebiasis comprising:

culturing trophozoites of Entamoeba histolytica axenically;

lyophilizing said trophozoites;

extracting an insoluble fraction from the trophozoites with polar solvents;

drying the insoluble fraction to eliminate residues of the solvents;

suspending the dried fraction in a buffer;

heating the buffered suspension for a sufficient time and at a sufficient temperature to yield preserved Entamoeba histolytica antigens (IC:MC) without the presence of enzymatic inhibitors, wherein said antigens are stable for at least six months;

separating the preserved antigens on SDS-PAGE to obtain an antigenic pattern of the preserved antigens;

electrotransferring the antigenic pattern of the preserved antigens to at least three membranes;

incubating one of the membranes with a sample of human serum from a patient diagnosed as having invasive amebiasis, incubating another one of the membranes with a sample of human serum from a patient diagnosed as having intestinal amebiasis, and incubating another one of the membranes with a sample of human serum from a patient diagnosed as being negative for any clinical symptoms of or for diagnostic tests of any amebic disease, wherein said incubations are performed for a sufficient period of time and under sufficient conditions to allow antibody-antigen binding;

detecting the antibody-antigen binding;

correlating the detected antibody-antigen binding on the electrotransferred membranes to the corresponding protein bands in the antigenic pattern of the preserved antigens;

identifying the antigens which result in positive antibody-antigen binding with each of the samples of human serum; and determining the antigens which are positive only with the sample of human serum from the patient diagnosed as having invasive amebiasis and which are negative with the sample of human serum from the patient diagnosed as having intestinal amebiasis and with the sample of human serum from the patient diagnosed as being negative for any clinical symptoms of or for diagnostic tests of any amebic disease in order to provide an antigenic reference pattern of the proteins selectively recognized by sera from patients with invasive amebiasis.

7. The method of claim 6, wherein the antigens positive only with the sample of human serum from the patient diagnosed as having invasive amebiasis have a relative molecular weight in kDaltons of 8, 9, 10, 11, 23, 25, or 37.

8. The method of claim 6, wherein the polar solvent is chloroform, methanol, ether, ethanol or mixtures thereof.

9. The method of claim 8, wherein the polar solvent is a mixture of chloroform and methanol.

10. A method of aiding in the differential diagnosis of a patient with invasive amebiasis by detecting the presence of antibodies in a sample of human serum which bind to *Entamoeba histolytica* antigens identified in an antigenic reference pattern as selectively recognized by sera from patients with invasive amebiasis comprising:

culturing trophozoites of *Entamoeba histolytica* axenically;

lyophilizing said trophozoites;

extracting an insoluble fraction from the trophozoites with polar solvents;

drying the insoluble fraction to eliminate residues of the solvents;

suspending the dried fraction in a buffer;

heating the buffered suspension for a sufficient time and at a sufficient temperature to yield preserved *Entamoeba histolytica* antigens (IC:MC) without the presence of enzymatic inhibitors, wherein said antigens are stable for at least six months;

separating the preserved antigens on SDS-PAGE to obtain an antigenic pattern of the preserved antigens;

electrotransferring the antigenic pattern of the preserved antigens to a membrane;

incubating the membrane with the sample of human serum for a sufficient period of time and under conditions sufficient to allow antibody-antigen binding;

detecting the antibody-antigen binding;

correlating the detected antibody-antigen binding on the electrotransferred membrane to the corresponding protein bands in the antigenic pattern of the preserved antigens; and identifying the samples of human serum containing antibodies which bind to at least one *Entamoeba histolytica* antigen identified in an antigenic reference pattern as selectively recognized by sera from patients with invasive amebiasis.

11. The method of claim 10, wherein the *Entamoeba histolytica* antigens identified in an antigenic reference pattern as selectively recognized by sera from patients with invasive amebiasis have a relative molecular weight in kDaltons of 8, 9, 10, 11, 23, 25, or 37.

12. The method of claim 10, wherein the polar solvent is chloroform, methanol, ether, ethanol or mixtures thereof.

13. The method of claim 12, wherein the polar solvent is a mixture of chloroform and methanol.

14. A method of aiding in the differential diagnosis of a patient with intestinal amebiasis by detecting the presence of antibodies in a sample of human serum which bind to *Entamoeba histolytica* antigens identified in an antigenic reference pattern as indicative of both invasive amebiasis and intestinal amebiasis and but not identified in an antigenic reference pattern as selectively recognized only by sera from patients with invasive amebiasis comprising:

culturing trophozoites of *Entamoeba histolytica* axenically;

lyophilizing said trohozoites;

extracting an insoluble fraction from the trophozoites with polar solvents;

drying the insoluble fraction to eliminate residues of the solvents;

suspending the dried fraction in a buffer;

heating the buffered suspension for a sufficient time and at a sufficient temperature to yield preserved *Entamoeba histolytica* (IC:MC) without the presence of enzymatic inhibitors, wherein said antigens are stable for at least six months;

separating the preserved antigens on SDS-PAGE to obtain an antigenic pattern of the preserved antigens;

electrotransferring the antigenic pattern of the preserved antigens to a membrane;

incubating the membrane with the sample of human serum for a sufficient period of time and under conditions sufficient to allow antibody-antigen binding;

detecting the antibody-antigen binding;

correlating the detected antibody-antigen binding on the electrotransferred membrane to the corresponding protein bands in the antigenic pattern of the preserved antigens;

identifying the samples of human serum containing antibodies which bind to at least one *Entamoeba histolytica* antigen identified in an antigenic reference pattern as indicative of both invasive amebiasis and intestinal amebiasis;

further identifying the samples of human serum identified in the previous first identification step, containing antibodies which bind to at least one *Entamoeba histolytica* antigen identified in an antigenic reference pattern as selectively recognized only by sera from patients with invasive amebiasis; and selecting the samples of human serum as being indicative of a patient with intestinal amebiasis as said samples not being identified in the previous second identification step by binding to at least one *Entamoeba histolytica* antigen identified in an antigenic reference pattern as selectively recognized only by sera from patients with invasive amebiasis.

15. The method of claim 14, wherein the *Entamoeba histolytica* antigens identified in an antigenic reference pattern as indicative of both invasive amebiasis and intestinal amebiasis have a relative molecular weight in kDaltons of 150, 29, 21, 20, 17, 16, 14 or 13.

16. The method of claim 14, wherein the *Entamoeba histolytica* antigens identified in an antigenic reference pattern as selectively recognized only by sera from patients with amebic liver abscesses have a relative molecular weight in kDaltons of 8, 9, 10, 11, 23, 25, or 37.

17. The method of claim 14, wherein the polar solvent is chloroform, methanol, ether, ethanol or mixtures thereof.

18. The method of claim 17, wherein the polar solvent is a mixture of chloroform and methanol.

* * * * *

UNITED STATES PATENT AND TRADEMARK OFFICE
CERTIFICATE OF CORRECTION

PATENT NO. : 5,861,263
DATED : January 19, 1999
INVENTOR(S) : Maria S. Flores-Castañeda It is certified that error appears in the above-identified patent and that said Letters Patent is hereby corrected as shown below:

Column 4, line 35, change "rivanal" to --rivanol--.

Column 6, line 36, change "$1.00b^{-2}$" to --$1.00^b$--.

Column 7, line 28, change "if" to --of--.

Column 8, line 64, change "anti-$\underline{E}$" to read --to $\underline{E}$--.

Column 12, line 19, delete "was obtained".

Column 15, line 3, before "intestinal" insert --non-invasive--.

Column 15, line 7, before "amebic" insert -- invasive--.

Column 15, line 21, before "intestinal" insert --non-invasive--.

Column 15, line 24, before "amebic" insert -- invasive--.

Column 18, line 1, delete "amebic liver abscesses" and insert --invasive amebiasis--.

Signed and Sealed this

Fourth Day of July, 2000

Attest:

Q. TODD DICKINSON

*Attesting Officer*  *Director of Patents and Trademarks*